United States Patent [19]

Hagarty

[11] 4,302,615
[45] Nov. 24, 1981

[54] SYNTHESIS OF 2-ALKOXYPHENOLS

[75] Inventor: John D. Hagarty, Sturtevant, Wis.

[73] Assignee: S. C. Johnson & Son, Inc., Racine, Wis.

[21] Appl. No.: 175,475

[22] Filed: Aug. 5, 1980

[51] Int. Cl.³ .................. C07C 41/01; C07C 41/28
[52] U.S. Cl. .................................................. 568/652
[58] Field of Search ..................................... 568/652

[56] References Cited

PUBLICATIONS

Eliel et al., J.A.C.S., vol. 84 (1962), 2371–2377.
Arnold et al., J.A.C.S. vol. 64 (1942), 1410–1413.

Primary Examiner—Bernard Helfin

[57] ABSTRACT

A reductive hydrogenolysis of a 2-substituted 1,3-benzodioxole is carried out employing a hydride-donating reducing agent system to produce a 2-alkoxyphenol.

8 Claims, No Drawings

SYNTHESIS OF 2-ALKOXYPHENOLS

BACKGROUND OF THE INVENTION

This invention relates to a process for preparing 2-alkoxyphenols from alkyl-1,3 benzodioxoles. In particular, it relates to a process for the selective reductive hydrogenolysis of a 2,2-dialkyl-1,3-benzodioxole employing a hydride reducing agent to form a 2-isoalkoxyphenol.

A class of intermediate compounds which has received industry wide attention are the 2-alkoxyphenols. Such compounds are useful, for example, in the preparation of insecticides. In particular, 2-isopropoxyphenol is a key intermediate in the preparation of the insecticide, 2-isopropoxy-1-phenoxy-N-methylcarbonamide.

Traditional methods for synthesizing 2-alkoxyphenols utilized the direct alkylation of catechol with a secondary halide, such as 2-bromopropane or 2-chloropropane. However, this reaction is undesirable for industrial purposes, due to the relatively low halide reactivity and the susceptibility of the catechol to dialkylation, rather than monoalkylation. In general, yields less than 30% of the theoretical amount are obtained employing direct alkylation with secondary halides.

It is known that in the presence of acidic agents, the compound lithium aluminium hydride reductively cleaves certain alicyclic acetals and ketals, known as 1,3-dioxolanes and 1,3-dioxanes, to their corresponding hydroxy ethers, B. Leggetter et al., Can. J. Chem. 43, 1030 (1964); Can. J. Chem 42, 990 (1964); Can. J. Chem. 42 1005 (1964): E. Eliel et al., J. Am. Chem. Soc. 84, 2371 (1962); J. Org. Chem. 30, 2441 (1965) and J. Am. Chem. Soc., 84, 2377 (1962). It is also known that the catalytic hydrogenation of certain acidified alkyl and cycloalkyl ketals provides saturated ether alcohols, Howard et al., J. Org. Chem. 26, 1026 (1959).

However, such reductive cleavage or catalytic hydrogenation has not heretofore been applied to benzodioxoles to selectively produce alkoxyphenols. It has been recognized in the art that benzodioxoles are particularly stable to acids and bases. Accordingly, it was not expected that benzodioxoles would be susceptible to a selective reductive hydrogenolysis to provide an etherified phenol. Attempts to ring-open benzodioxoles and to selectively catalytically hydrogenate them to produce an etherified phenol have been unsuccessful. It has been found that in the case of benzodioxoles, both C-O bonds are cleaved, but the molecule is very resistant to hydrogenolysis, R. T. Arnold et al., J. Am. Chem. Soc., 64, 1410 (1942).

It is accordingly, an object of this invention to provide a process for selectively ring-opening and hydrogenating an alkyl substituted, 1,3-benzodioxole to produce high yields of a 2-alkoxyphenol.

SUMMARY OF THE INVENTION

The above and other objects are met by conducting a reductive hydrogenolysis of a 2-alkyl-1,3-benzodioxole with a hydride-donating reducing agent system to produce a 2-alkoxyphenol. The hydride-donating reducing agent system may be (i) a metal hydride in the presence of a Lewis acid, (ii) a metal hydride which does not require a Lewis acid catalyst, such as diisobutyl aluminim hydride or (iii) a hydride donor in an ionic hydrogenation system, such as a silane and a proton donor system.

The present process provides high yields of the desired selectively hydrogenated product, a 2-alkoxyphenol, at low temperatures with minimal undesired by-products.

DETAILED DESCRIPTION OF THE INVENTION

The starting materials for the invention are 2-alkyl-1,3-benzodioxoles, preferably 2,2-dialkyl-1,3-benzodioxoles. Typical starting materials are of the formula:

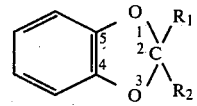

wherein $R_1$ and $R_2$ are the same or different and $R_1$ is H or lower alkyl and $R_2$ is lower alkyl. Preferably, $R_1$ and $R_2$ are each lower alkyl and, especially, $C_1$–$C_3$ alkyl groups.

The particularly preferred starting compound is 2,2-dimethyl-1,3-benzodioxole.

The preparation of the 2-substituted-1,3-benzodioxole starting compounds is known to the art. For example, catechol is subjected to dehydration and the resulting mixture is treated with para-toluenesulfonic acid. Thereafter, dimethoxypropane or another dialkoxyalkane within the ambit of this invention is added to this mixture and the final reaction mix is heated to distill off methanol and drive to reaction to completion. The resulting product is isolated as 2,2-dimethyl-1,3-benzodioxole. It is also possible to condense catechol with a ketone, using $P_2O_5$, directly, employing a dehydrating agent to drive off water and to thereby form the desired dioxole starting product.

The hydride-donating reducing agent capable of initiating the reductive hydrogenolysis is also adapted to selectively cleave the dioxole ring. Typical hydride-donating reducing agents employed for this purpose are metal hydrides, particularly alkali metal hydrides, especially lithium aluminum hydride, sodium hydride, lithium triethyl borohydride, lithium hydride, sodium aluminum hydride, sodium borohydride, sodium diethyl aluminum hydride, sodium bis (2-methoxy ethoxy) aluminum hydride and the like and mixtures thereof.

For enhanced results the reducing agent system includes a Lewis acid, particularly, a strong Lewis acid, such as aluminum trichloride, titanium tetrachloride, boron trifluoride, and the like, and mixtures thereof. It is postulated that the Lewis acid functions to coordinate with the oxygen bond of the dioxole, thus weakening the C-O bond. It has been hypothecated that the hydride attacks the 2-carbon position of the dioxole ring and adds to it, thus cleaving the C-O bond as follows:

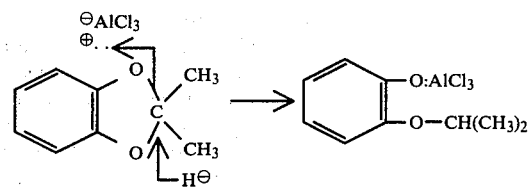

The cleaved oxygen then adds a proton to yield the etherified phenol intermediate.

In general, the weight ratio of hydride (metal hydride, silicon hydride, etc) to dioxole may vary broadly. The hydride is employed in a molar ratio sufficient to provide the desired yield. Generally, increasing the molar ratio of hydride to dioxole increases the yield of dioxole. For enhanced yields it is preferred that the molar ratio of hydride to dioxole is at least about 0.5:1, preferably at least about 1:1. It is seldom necessary to employ a molar ratio greater than about 2:1. Higher ratios are usually wasteful of costly hydride and, accordingly, are unnecessary.

The weight ratio of Lewis acid to dioxole can vary widely. Sufficient Lewis acid is employed to weaken the C-O bond. For best results, it is preferred that the molar ratio of Lewis acid to dioxole is at least about 0.5:1 and preferably at least about 1:1. Yields of product are increased as the molar ratio of Lewis acid to dioxole is increased. In general, it is unnecessary to employ a molar ratio greater than about 2:1.

It has been found that satisfactory yields can be obtained in the absence of Lewis acids, when the hydride donating reducing agent system is simply diisobutylaluminum hydride.

In addition, when silicon hydrides (silanes) and a proton donor are employed as the hydride donor reducing agent system, the reaction route is postulated to be a ionic hydrogenation as follows:

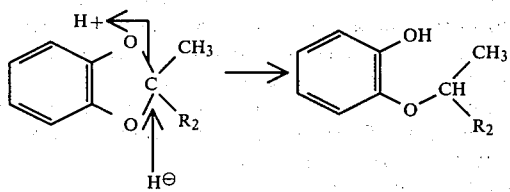

A proton donor is preferably utilized with the silicon hydrides to provide the enhanced yields. Preferred silicon hydrides are trialkyl silicon hydrides, particularly triethyl silane. The proton donor may be a strong acid, preferably trifluoroacetic acid. Such systems are known to the art.

The proton donor is preferably employed in amounts sufficient to dissolve the mixture of silicon hydride and starting material. For this and other purposes it is preferred to employ a molar ratio of proton donor to the total moles of silane and dioxole of at least about 1.5:1.

For best results the reductive hydrogenolysis reaction is carried out in the presence of a solvent in which the starting material and the reducing agent are soluble. In general, inert organic solvents are utilized. Typical solvents include aromatic and aliphatic solvents, such as ethyl ether, benzene, toluene, tetrahydrofuran, dioxane, diethylene glycol dimethyl ether, xylene, mixtures thereof, and the like. Inert paraffinic solvents may be also be employed.

The reaction rate is influenced to a minor degree by the reaction temperature. The reaction temperature exhibits no appreciable effect on the reaction yield, however. In general, the reaction temperature is from about 0° C. to 60° C. depending, in part, on the nature of the solvent selected and the rate of addition of the dioxole to the hydride reducing agent. For most reaction systems the hydrogenolysis reaction is complete in from 2 to 10 hours, depending upon the reducing agent selected and reaction temperature selected.

The following examples illustrate certain preferred embodiments of the invention and are not limitative of scope.

PREPARATION EXAMPLE 1

Preparation of the preferred starting material, 2,2-dimethyl-1,3-benzodioxole, is illustrated as follows:

To a solution containing 220 g. (2.0 moles) of catechol in 2 liters of benzene and 1.0 g. of camphorsulfonic acid, there was added 250 g. (2.4 moles) of 2,2-dimethoxypropane. The mixture was heated during the addition and the methanol formed was removed by distillation along with a portion of the benzene up to a head temperature of 58° C. through a column packed with glass helices. The remaining volatiles are then removed after neutralization of the catalyst with 1.5 g. of sodium methoxide. The product is purified by distillation, b.p. 85° C. (1 mm).

EXAMPLE 1

The preparation of 2-isopropoxyphenol employing a metal hydride-Lewis acid system was carried out by placing 13.3 grams (0.1 mole) of a anhydrous aluminum trichloride in a three-necked flask equipped with a mechanical stirrer, a condenser with a drying tube and an addition funnel. Thereafter, 100 ml of chilled ether was cautiously added to dissolve the aluminum trichloride, while simultaneously cooling the flask in an ice bath. The, 25 ml (0.025 moles) of a 1 M solution of lithium aluminum hydride was added dropwise, with cooling. Thirty minutes later, 8.0 g (0.054 moles) of 2,2-dimethyl-1,3-benzodioxole, predissolved in ether, was added dropwise with continued stirring and cooling. The mixture was then allowed to warm to room temperature. The reaction was completed by refluxing the mixture for two hours.

The reaction product was isolated by cooling, hydrolyzing with 10% sulfuric acid and extracting with ether. The yield was 7.8 g (97.5%) of crude 2-isopropoxyphenol, which was 90% pure, according to gas chromatography. Actual yield was 88%. Other 2-alkoxyphenols are prepared in accordance with the procedure substituting a desired benzodioxole of the invention.

EXAMPLE 2

The preparation of 2-isopropoxyphenol from 2,2-dimethyl-1,3-benzodioxole by reduction with diisobutylaluminum hydride is illustrated as follows:

In a dry 3-neck flask equipped with a stirrer, a condenser, a nitrogen inlet and rubber septum, there was placed, by means of a syringe, 33.0 ml. (0.055 moles) of diisobutyl aluminum hydride in toluene. About 30 ml. of additional dry toluene was added. Then, a toluene solution of 7.5 g. (0.05 mole) of 2,2-dimethyl-1,3-benzodioxole was added, dropwise. The resulting mixture was then heated at 60°-70° for 4 hours and allowed to stand at room temperature, overnight. Excess hydride was destroyed by careful addition of methanol, followed by water and 6 N sulfuric acid. The organic layer containing the desired product separated from the water layer. Thereafter, the water layer was washed four times with toluene. The combined toluene extracts were dried over magnesium sulfate. Evaporation of the toluene solvent gave 8.0 g. of 2-isopropoxyphenol, which was 67.2% pure, according to gas chromography. The yield was 72% theoretical.

EXAMPLE 3

The preparation of 2-isopropoxyphenol via ionic hydrogenation of 2,2-dimethyl-1,3-benzodioxole is exemplified in the preparation set forth below:

In a 3-neck flask equipped with a stirrer, an addition funnel and a reflux condenser, there was placed a mixture of 28.0 g. (0.24 mole) of triethyl silane and 30.0 g. (0.2 mole) of 2,2-dimethyl-1,3-benzodioxole. To this mixture there was added, at room temperature, 68.4 g. (0.6 mole) of trifluoroacetic acid. The temperature of the reaction mixture rapidly rose to 60° C. The reaction temperature was maintained at 50°-60° for 3 hours. After cooling, the reaction mixture was washed several times with aqueous sodium bicarbonate to remove trifluoroacetic acid. The product was isolated by ether extraction. The yield of 2-isopropoxyphenol was 81.6%.

EXAMPLE 4

The use of sodium borohydride as a reducing agent is demonstrated in the following test run in which 0.1 mole of aluminum trichloride (13.3 g.) was placed in a three-necked flask and reacted with 0.022 moles of sodium borohydride and 0.054 moles of 2,2-dimethyl-1,3-benzodioxole in accordance with the procedure of Example 1. The solvent was diethylene glycol monomethyl ether. The actual yield of 2-isopropoxyphenol was 56%.

EXAMPLE 5

Preparation of 2-isopropoxyphenol using sodium diethyl aluminum hydride and aluminum trichloride is illustrated in this example in which in a 250 ml 3-neck flask equipped with a stirrer, a condenser with drying tube and a rubber septum with a nitrogen inlet there was placed (by syringe) 0.055 moles of sodium diethyl aluminum hydride. Next, a toluene solution of 8.0 g. (0.053 mole) of 2,2-dimethyl-1,3-benzodioxole was added by syringe. No heat was evolved. A suspension of 10 g. of aluminum trichloride in toluene was then added gradually. Heat was evolved and a white precipitate formed. The mixture was then refluxed for 4 hours and allowed to stand overnight. Methanol, water and 6 N sulfuric acid were added in that order and the organic and water layers separated. The aqueous solution was extracted twice with ether and the combined organic layers were dried and evaporated to give 13.3 g of crude product. The purity of the 2-isopropoxyphenol according to gas chromatography was 53.2%. The actual yield was 88%.

EXAMPLE 6

Preparation of 2-isopropoxyphenol employing sodium bis(2-methoxy ethoxy) aluminum hydride as the hydride donor is exemplified in the following test:

In a dry 3-neck flask equipped with a stirrer, a condenser, a nitrogen inlet and rubber septum, there was placed a mixture of 10 g of aluminum trichloride and 50 ml. of dry toluene. To this mixture was added, by means of a syringe, 0.055 moles of sodium bis(methoxy ethoxy)aluminum hydride. Next, a toluene solution of 8.0 g. (0.053 mole) of 2,2-dimethyl-1,3-benzodioxole was added dropwise with the aid of a syringe. A minor amount of heat was evolved. The reaction mixture was then heated to 70°-80° C. for 4 hours. The workup of Example 5 was carried out on the crude product to give a crude yield of 9.0 g., which was 69.5% pure according to gas chromatography. The actual yield of 2-isopropoxyphenol was 78%.

2-isopropoxyphenol is converted to the desired pesticide by reaction with N-methylisocyanate as follows:

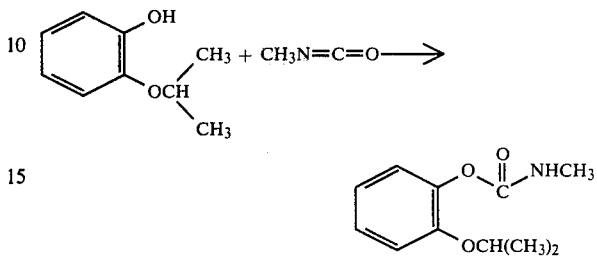

Other embodiments and variations will be apparent from this disclosure to those with ordinary skill in the art. This invention is not to be limited except as set forth in the following claims:

What is claimed is:

1. Process for producing a 2-alkoxyphenol of the formula

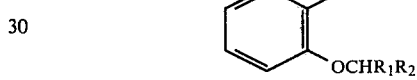

which comprises: conducting a reductive hydrogenolysis with a metal hydride in the presence of a Lewis acid of a 2-alkyl-1,3-benzodioxole of the formula:

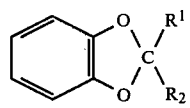

wherein $R_1$ and $R_2$ are the same or different and $R_1$ is H or lower alkyl and $R_2$ is lower alkyl.

2. Process for producing 2-isopropoxyphenol comprising: conducting a reductive hydrogenolysis of 2,2-dimethyl-1,3-benzodioxole with a metal hydride in the presence of a Lewis acid.

3. The process of claim 1 wherein the reaction is carried out in an inert organic solvent.

4. The process of claim 1 wherein the reaction temperature is from about 0° C. to 60° C.

5. The process of claim 1 wherein the reaction is carried out in from about 2-10 hours.

6. The process of claim 1 wherein the molar ratio of hydride to 1,3-benzodioxole is at least about 0.5:1.

7. The process of claim 2 wherein the molar ratio of Lewis acid to 1,3-benzodioxole is at least about 0.5:1.

8. The process of claim 2 wherein the hydride is selected from lithium aluminum hydride, sodium borohydride, sodium diethyl aluminum hydride and sodium bis(2-methoxy ethoxy) aluminum hydride and the Lewis acid is aluminum trichloride.

* * * * *